United States Patent

Suzuki et al.

Patent Number: 6,065,687
Date of Patent: May 23, 2000

[54] SUSTAINED RELEASE PREPARATIONS

[75] Inventors: Hiroshi Suzuki; Noboru Aiba; Ryuichi Saguchi, all of Niigata; Kinya Ogawa, Tokyo; Kenichi Itoh, Niigata, all of Japan

[73] Assignee: Shin-Etsu Chemical Co., Ltd., Tokyo, Japan

[21] Appl. No.: 08/679,262

[22] Filed: Jul. 12, 1996

Related U.S. Application Data

[63] Continuation-in-part of application No. 08/421,323, Apr. 13, 1995, abandoned.

[30] Foreign Application Priority Data

May 24, 1994 [JP] Japan ................................ 6-109643
Jul. 13, 1995 [JP] Japan ................................ 7-177538

[51] Int. Cl.$^7$ ............................................. A61L 9/04
[52] U.S. Cl. ............................................. 239/44; 239/34
[58] Field of Search ............................ 239/34, 35, 37, 239/43, 44, 57; 43/125, 131; 428/905

[56] References Cited

U.S. PATENT DOCUMENTS

| | | |
|---|---|---|
| 3,698,974 | 10/1972 | Rabussier et al. . |
| 4,160,335 | 7/1979 | Von Kohorn et al. ................... 43/131 |
| 4,834,745 | 5/1989 | Ogawa et al. . |
| 4,932,155 | 6/1990 | Friemel et al. ........................... 43/125 |
| 5,071,704 | 12/1991 | Fischel-Ghodsian . |
| 5,219,121 | 6/1993 | Fox et al. . |
| 5,359,808 | 11/1994 | Fitsakis ..................................... 43/131 |

FOREIGN PATENT DOCUMENTS

| | | |
|---|---|---|
| 0273197 | 7/1988 | European Pat. Off. . |
| 0 342 126 | 11/1989 | European Pat. Off. ....... A01N 25/18 |
| 0 683 977 | 11/1995 | European Pat. Off. ......... A01M 1/20 |
| 6-88886 | 9/1988 | Japan ............................ A01N 25/18 |
| 2-96502 | 4/1990 | Japan ............................ A01N 25/18 |
| 9300115 | 1/1993 | WIPO . |

Primary Examiner—Lesley D. Morris
Attorney, Agent, or Firm—Sughrue, Mion, Zinn, Macpeak & Seas, PLLC

[57] ABSTRACT

Herein disclosed is a sustained release dispenser capable of uniformly releasing a volatile liquid ingredient over a long time period even when the amount of the liquid ingredient remaining in a container is reduced. According to an embodiment, the sustained release dispenser comprises a plastic container 4 having a liquid and volatile ingredient-permeable outer layer 1 and a liquid-absorbable inner layer 3 having the same material as those of the outer layer 1 and a liquid and volatile ingredient 2 enclosed in the plastic container. According to other embodiment, the sustained release dispenser comprises a plastic container 6 in which grooves 5 are formed on the inner wall and a volatile ingredient 2 accommodated in the container 6. According to other embodiment, the sustained release dispenser comprises a bag formed from a liquid permeable film 7 provided with a highly wettable film 8 on the inner surface thereof and a liquid sex pheromone 9 accommodated in the bag.

3 Claims, 3 Drawing Sheets

SUSTAINED RELEASE PREPARATIONS

This is a continuation-in-part application of application Ser. No. 08/421,323 filed on Apr. 13,1995 now abandoned.

BACKGROUND OF THE INVENTION

The present invention relates to a sustained release preparation which permits gradual release of volatile ingredients such as pheromones, repellents, perfumes and insecticides and which is effective, in particular, as a sustained release dispenser for releasing pheromones to control occurrence of harmful insects.

There has been required for the development of a pharmaceutical or agricultural dispenser which permits gradual release of a volatile ingredient to ensure a long lasting effect thereof. The mating disruption method must satisfy this requirement, this method is utilized for control of agriculturally harmful insects through release of, for instance, a sex pheromone at a predetermined concentration over a long time period. The term "mating disruption method" herein means a method comprising, 1) making a sex pheromone drift in fields at a concentration substantially higher than that released from harmful insects, 2) to thus lower the communication ability of the harmful insects such as an ability of male or female insects to recognize the individual opposite sex and to confirm the positions thereof, 3) and to thereby disturb mating of the insects. There has been used a sustained release dispenser containing a pheromone as a physiologically active substance of a harmful insect as a communicationdisturbing agent. Such sustained release dispenser may be in various forms, for instance, those packed in microcapsules as disclosed in U.S. Pat. Nos. 2,800,457, 2,800,458 and 3,577,515; those supported by carriers as disclosed in U.S. Pat. No. 4,160,335; those packed in tubes as disclosed in U.S. Pat. Nos. 4,600,146 and 4,834,745; or those packed in bottle-like containers as disclosed in European Patent No. 273,197. The sustained release dispenser packed in a container having a large capacity, i.e., a reservoir type one is one of the leading mainstream thereof.

Containers for such reservoir type sustained release dispensers have been produced from a variety of plastics selected depending on the physical properties of individual volatile ingredients. When using such a reservoir type dispenser, a liquid and volatile ingredient absorbed in the plastic wall of the container can be vaporized from the outer surface thereof and diffuse into the air. Therefore, the release rate thereof is approximately proportional to the outer surface area of the reservoir which absorbs the liquid ingredient. The release rate has conventionally been controlled by adjusting the size of the outer surface area through appropriate selection of plastic materials for the reservoir and shapes thereof. However, the reservoir type sustained release dispenser suffers from a problem in that the amount of the liquid remaining in the reservoir decreases as the ingredient is released and this results in a decrease of the surface area wetted with the liquid ingredient through absorption thereof and hence the reduction in the amount of the drug released therefrom during the latter half of the ingredient-release, as clearly described in J. Economical Entomology, 78, No. 6, 1985.

SUMMARY OF THE INVENTION

The present invention has been developed for solving the foregoing problems associated with the conventional techniques and accordingly, it is an object of the present invention to provide a sustained release dispenser which permits uniform release of a volatile ingredient over a long time period even if the amount of the liquid ingredient remaining in a container is reduced.

According to the present invention, the foregoing object can effectively be accomplished by providing a sustained release dispenser comprising a volatile liquid ingredient in a plastic container having means for making a liquid absorbable and permeable.

DETAILED EXPLANATION OF THE INVENTION

Figure 1:
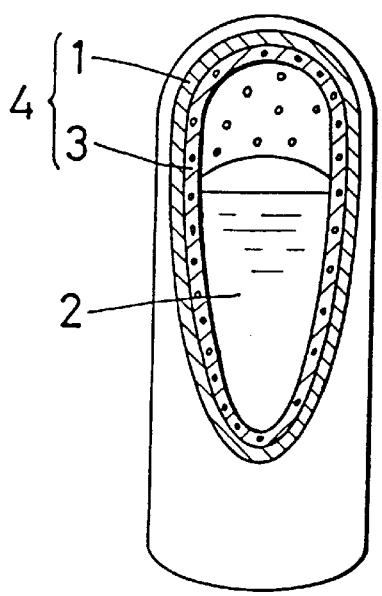
FIG. 1 is a cross-sectional perspective view illustrating main parts of an embodiment of the sustained release dispenser according to the present invention.

As will be seen from FIG. 1, the sustained release dispenser of the present invention comprises a plastic container 4, which has a liquid and volatile ingredient-permeable outer layer 1 and a liquid-absorbable inner layer 3 having properties identical to those of the outer layer 1, and a liquid and volatile ingredient 2 accommodated in the plastic container 4.

The inner layer 3 is a porous layer and the pores thereof are communicated to one another. The inner layer 3 can be prepared by extrusion molding in which the volatile ingredient 2 is incorporated into the layer when a molten plastic is extrusion-molded, or by foam extrusion-molding.

Figure 2:
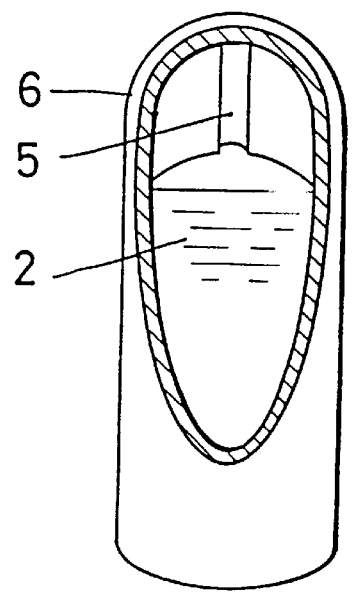
FIG. 2 is a cross-sectional perspective view illustrating main parts of other embodiment of the sustained release dispenser according to the present invention.

Other embodiment of the sustained release dispenser according to the present invention comprises, as shown in FIG. 2, a container 6 and a volatile ingredient 2 accommodated therein. A (plural) groove(s) is/are formed through from bottom end to top end on the inner wall of the container.

Materials used for preparing the plastic containers 4 and 6 may, for instance, be polyolefins such as polyethylenes and polypropylenes; ethylenevinyl acetate copolymers; ethylene-acrylic acid ester copolymers; and ethylene-methacrylic acid ester copolymers. These raw materials may be used alone or in any combination. These plastic materials each is formed into a tube or bottle through extrusion molding or blow molding, which serves as an outer layer 1.

The volatile ingredient 2 may, for instance, be a sex pheromone. The sex pheromone is released through the container 4 or 6 to thus control any occurrence of agriculturally harmful insects.

The volatile ingredient 2 accommodated in the container 4 penetrates into the whole inner layer 3 through absorption in fine pores of the inner layer 3, then penetrates into the outer layer 1 through the inner layer and is finally released in the air from the surface of the outer layer 1. The ingredient 2 is absorbed in the whole inner layer 3 and hence penetrates into the whole outer layer 1 even if the liquid level of the ingredient 2 accommodated in the container 4 is lowered as the ingredient is released and therefore, the amount of the ingredient released from the container 4 is maintained at a constant level.

On the other hand, the ingredient 2 in the container 6 ascends along the groove 5 due to the capillary action, is absorbed in the container 6 and then released in the air from the outer surface of the container 6. Accordingly, the ingredient 2 ascends along the grooves 5, while being absorbed in the container 6 and released in the air even if the liquid level of the ingredient 2 accommodated in the container 6 is lowered as the release of the ingredient proceeds and therefore, the amount of the ingredient released from the container 6 is also maintained at a constant level.

Figure 6:
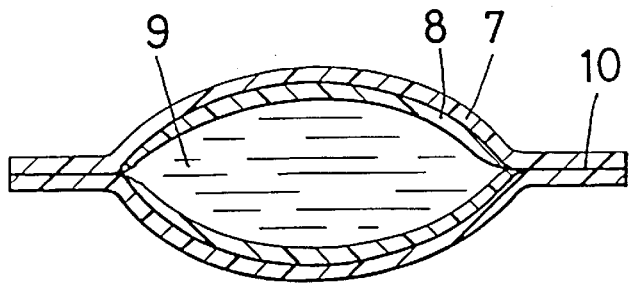
FIG. 6 is a cross-sectional illustrating of other embodiment of the sustained release dispenser according to the present invention.

As will be seen from FIG. 6, the sustained release dispenser of the present invention comprises a bag formed from a liquid permeable film 7 provided with a highly wettable film 8 on the inner surface thereof and a liquid sex pheromone 9 accommodated in the bag.

The highly wettable film 8 is preferably set up on one or both sides of the inner wall of the bag.

The highly wettable film 8 is preferably selected from the group consisting of nonwoven fabrics of polypropylenes, polyethylenes, polyesters and nylons; nonwoven fabrics of polyolefin species consisting of binary materials which comprise a core material of a polyester or nylon; and porous films of polyesters, nylons, polysulfones, polyethylenes and polypropylenes, which may be used alone or in any combination.

The highly wettable film 8 set up on the inner wall of the bag is always wetted with the liquid sex pheromone 9 due to the capillary action thereof and this, in turn, always ensures the contact between the liquid permeable film 7 constituting the bag and the liquid sex pheromone 9.

Preferred embodiments of the present invention will hereunder be described in more detail, but the present invention is by no means limited to these specific embodiments.

FIG. 1 is a cross-sectional perspective view illustrating main parts of an embodiment of the sustained release dispenser according to the present invention. The sustained release dispenser is prepared by charging a pheromone as a volatile ingredient 2 in a hollow tube-like container 4 which comprises a plastic outer layer 1 and a plastic inner layer 3 and then sealing the container 4 by heat to thus enclose the ingredient 2 therein.

The inner layer 3 is a porous layer whose pores are communicated to one another. The porous layer may be prepared by the following methods. A first method comprises the step of injecting a volatile ingredient 2 compatible with a plastic material during extrusion molding the plastic into the porous layer. The temperature for the extrusion molding varies depending on the kinds of plastics, but in general ranges from about 130 to 300° C. For this reason, pheromones each having a boiling point of not less than 170° C. can be used in the invention. The plastic is hardened while the plastic in the molten state comes in contact with the pheromone in this method and accordingly, the outer and inner layers 1 and 3 are produced from the same kind of plastics. The porous layer, i.e., the inner layer 3 has a thickness ranging from about 0.02 to 0.05 mm. This method permits the molding of the inner layer simultaneously with the charging of the pheromone and it is thus the most suitable method for mass production of the sustained release dispensers.

A second method is a molding method which makes use of the foam extrusion technique. The molding through foam extrusion comprises the step of simultaneously extruding both outer and inner layers in such a manner that a foaming agent-containing plastic is molded into an inner layer 3 and the plastic free of foaming agent is molded into an outer layer 1. The thickness of the porous layer serving as the inner layer 3 suitably ranges from 0.01 to 0.10 mm. The foaming agents usable herein may be, for instance, heat decomposable compounds such as azo compounds and volatile solvents such as hydrocarbons.

The size of the tube preferably has an inner diameter ranging from 0.5 to 4 mm, a thickness ranging from 0.1 to 2 mm and a length of not less than 50 mm because of easiness of production and easy handling. In this respect, if metal wires are fitted to the tube in parallel thereto, the tube can easily be bent and attached to plant bodies. The metal wire may be selected from those easily bendable and free of restoration through the elastic action, such as aluminum, copper and iron wires.

The tube is produced by extruding a molten plastic through a die, while supplying air to a mandrel positioned at the center of the die.

A bottle-like container is produced in the same way as the tube-like container. The surface area of the bottle-like container is smaller compared with that of the tube-like container, therefore the release rate of the ingredient 2 is correspondingly lowered. For this reason, the bottle-like container is suitable for accommodating an ingredient having relatively high volatility. The thickness of the bottle ranges from 0.1 to 2 mm like the foregoing tube while taking into consideration, for instance, stable release of the ingredient. The bottle-like container is in general molded by the blow molding technique.

The ingredient 2 is absorbed in the inner layer 3, then penetrates into the outer layer 1 and is finally released in the air. The ingredient 2 such as a pheromone absorbed in the inner layer 3 penetrates into the outer layer 1 by itself. Therefore, the wet area of the tube is not reduced and accordingly, the ingredient-release rate is not likewise lowered.

FIG. 2 is a cross-sectional perspective view illustrating main parts of other embodiment of the sustained release dispenser according to the present invention. The sustained release dispenser according to this embodiment is prepared by charging a volatile ingredient 2 in a hollow tube-like container 6 in which grooves 5 are formed on the inner wall thereof and then fusing the tube 6 to thus enclose the ingredient 2 therein.

The grooves 5 present on the inner wall of the container can be formed through the use of a mandrel having projections. The width and depth of each groove 5 may vary depending on the shape of the container, but both of them range from about 0.01 to 0.5 mm. The number of the grooves 5 to be formed is preferably as much as possible, but at least one groove may ensure a desired effect of the invention. If the container is subjected to melt-molding, the molded container is hardened while reducing the size of the grooves 5. Therefore, the projections must have a size 2 to 3 times that of the final groove 5.

The volatile ingredient 2 is, for instance, a pheromone and the plastic material for the container is polyethylene as in the case of the sustained release dispenser shown in FIG. 1. Most of the ingredient accommodated in the tube penetrates into the outer layer of the tube through the inner layer thereof and is then released in the air, but a part of the ingredient ascends along the grooves 5 due to the capillary action and is released in the air in the same manner. Accordingly, the ingredient-release rate is not lowered even if the amount of the ingredient remaining in the tube is reduced.

FIG. 6 is a schematic cross sectional view of an embodiment of the sustained release dispenser according to the present invention. As seen from this figure, the dispenser according to this embodiment comprises a bag made from a liquid permeable film 7 provided with a highly wettable film 8 on both sides of the inner wall of the bag and a liquid sex pheromone 9 accommodated in the bag.

The sex pheromone 9 is absorbed by the highly wettable film 8 to thus wet the film 8 and subsequently penetrates into the liquid permeable film 7. The liquid sex pheromone 9 penetrated into the film 7 is evaporated through the outer surface of the bag and thus released into the open air.

The sustained release dispenser is prepared as follows. Highly wettable films 8 are adhered to one side each of two liquid permeable films 7 except for the portion 10 at which these liquid permeable films 7 are ultimately sealed to give two sheets provided with the highly wettable film 8, followed by putting these sheets in layers in such a manner that the highly wettable films 8 face each other and closing the sheets at three sides through heat sealing to give a bag whose one side is opened. The liquid sex pheromone 9 is injected into the bag through the opening and then the opened side is closed through heat sealing.

Figure 7:
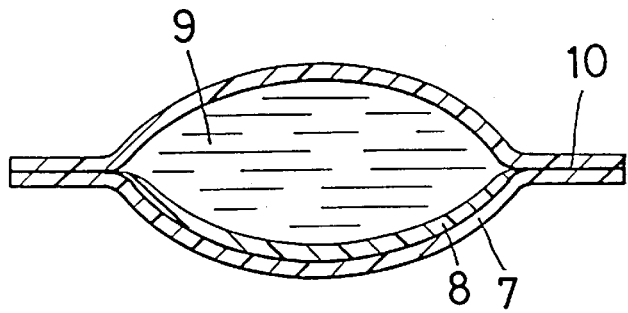
FIG. 7 is a cross-sectional illustrating of other embodiment of the sustained release dispenser according to the present invention.

Alternatively, the sustained release pheromone-containing preparation of the invention may comprise the highly wettable film 8 only on one side of the inner wall of the bag as shown in FIG. 7.

Moreover, the shape of the bag may be a four side-sealed bag, a three side-sealed bag, pillow-shaped packaging bag or a stick-like packaging bag.

EXAMPLE 1

When a high density polyethylene (hereunder simply referred to as "polyethylene") was extrusion-molded, Z,Z/E-7,11-hexadecadienyl acetate (hereunder referred to as "HDDA") which is the sex pheromone of pink bollworm was injected to form a hollow tube whose inner layer was a porous layer. More specifically, the method was carried out as follows.

The polyethylene was extruded through a die at 200° C., while injecting HDDA maintained at 150° C. through the mandrel positioned at the center of the die, then the extruded polyethylene was introduced into a water bath maintained at 70° C. to thus continuously mold a HDDA-charged tube having an inner diameter of 0.80 mm and a thickness of 0.32 mm(including a porous layer having a thickness of 0.02 mm). The resulting tube was sealed at equal lengths of 200 mm and then cut into individual sustained release dispensers each containing 80 mg of HDDA enclosed therein.

Figure 3:
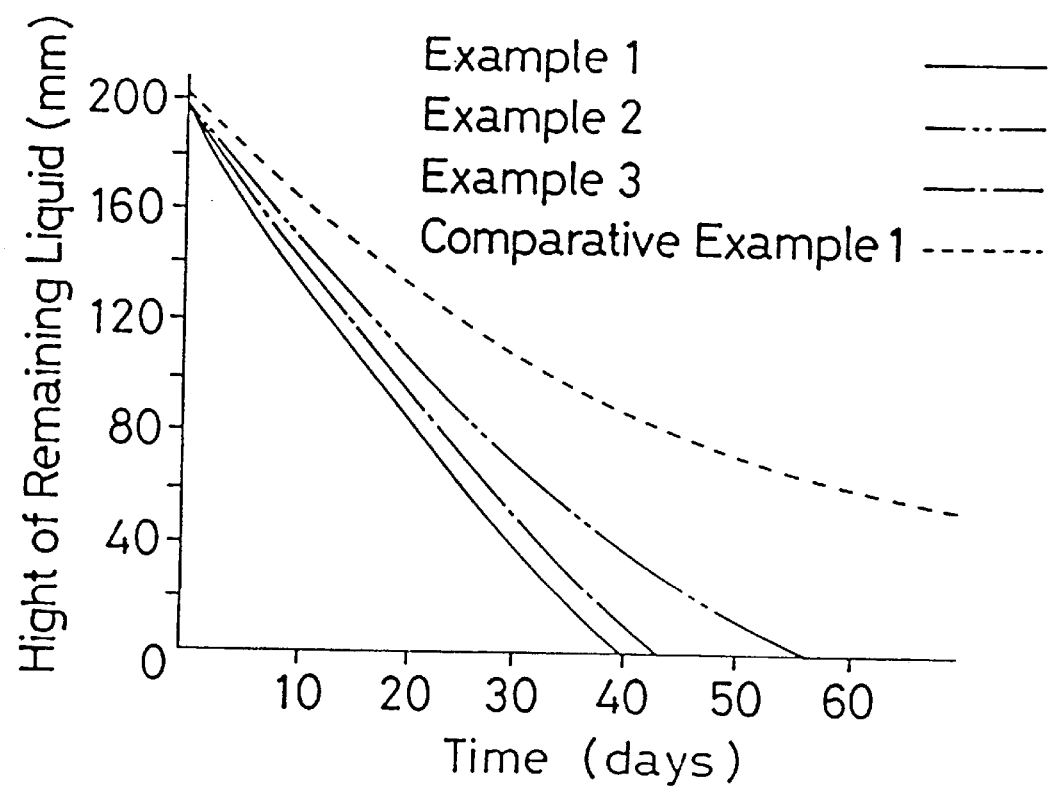
FIG. 3 is a diagram showing a change, with time, of the height of an HDDA liquid remaining in a tube.
Figure 4:
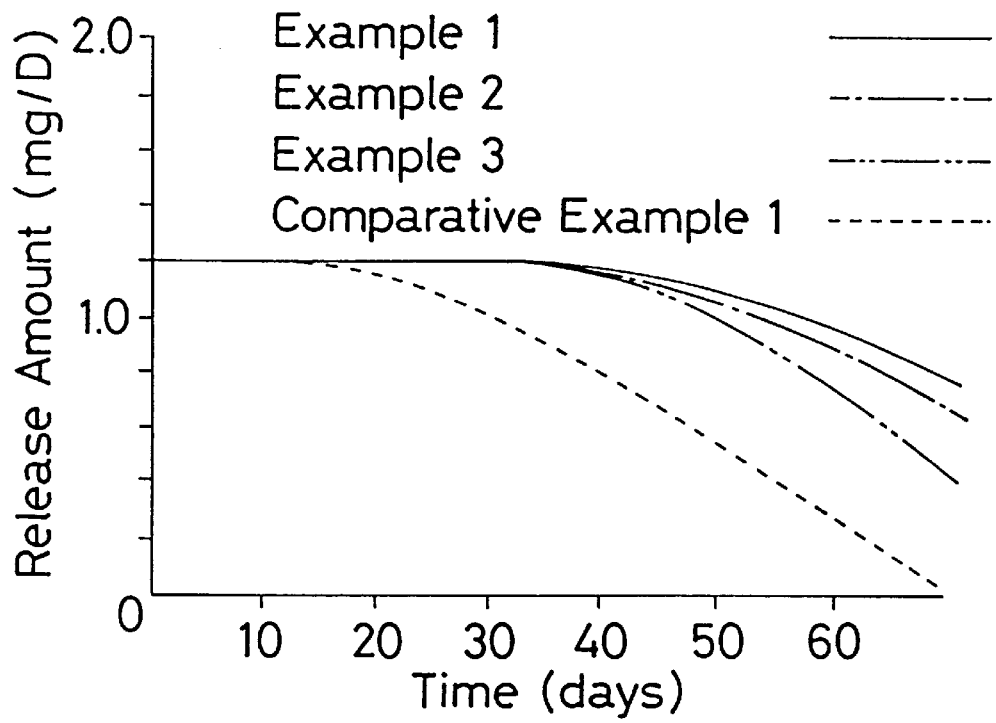
FIG. 4 is a diagram showing a change, with time, of the amount of released HDDA.

The dispenser was introduced into a thermostatic chamber maintained at 40° C. to determine the ingredient-release quality of the dispenser. FIG. 3 is a diagram showing a change, with time, of the height of the HDDA liquid remaining in the tube and FIG. 4 is a diagram showing a change, with time, of the amount of released HDDA. No liquid ingredient remained in the tube after 40 days as seen from FIG. 3, but the dispenser continued excellent release of HDDA even after 60 days as seen from FIG. 4. This was because a small amount of HDDA was still absorbed in the porous polyethylene layer. The rate of the remaining HDDA observed after 60 days was found to be 7%.

COMPARATIVE EXAMPLE 1

HDDA was introduced into a hollow tube whose inner wall was smooth and which had an inner diameter of 0.80 mm and a thickness of 0.30 mm. The conditions for the production of the hollow tube were identical to those used in Example 1 except that air of 20° C. was substituted for the HDDA used in Example 1 during extrusion of the polyethylene. HDDA was charged in the hollow tube for 3 hours at a pressure of 8 kg/cm$^2$, and the tube was sealed and then cut at a length of 200 mm. Individual sustained releases dispenser were prepared each containing 80 mg of HDDA enclosed therein.

The ingredient-release quality of the dispenser was examined in the same manner used in Example 1. The results thus obtained are plotted on FIGS. 3 and 4. There was observed marked reduction in the rate of ingredient-release with the lapse of time as seen from FIG. 4. At the same time, the reduction of the liquid remaining in the tube gradually became slower as seen from FIG. 3. The rate of the remaining HDDA observed after 60 days was found to be 25%.

EXAMPLE 2

In this Example, HDDA was charged in a hollow tube comprising porous inner layer formed through foam molding. The conditions for producing the hollow tube were identical to those used in Comparative Example 1 except that a polyethylene was extruded while azodicarbonamide as a foaming agent was added to a layer which would serve as the inner layer so that a porous layer formed had a thickness of 0.05 mm. The resulting tube was found to have an inner diameter of 0.80 mm and a thickness of 0.35 mm (including the porous layer having a thickness of 0.05 mm). The hollow tube was treated by the same method used in Comparative Example 1 to give sustained release dispensers each having a length of 200 mm and containing 80 mg of HDDA enclosed therein.

The ingredient-release quality of the dispenser was examined in the same manner used in Example 1. The results thus obtained are plotted on FIGS. 3 and 4. As seen from FIGS. 3 and 4, the ingredient-release quality of the dispenser was approximately identical to that of the dispenser produced in Example 1. The rate of the remaining HDDA observed after 60 days was found to be 10%.

EXAMPLE 3

A hollow tube was prepared by extrusion-molding a polyethylene in such a manner that grooves were formed on the inner wall of the resulting tube and then HDDA was charged therein. The conditions for the production of the hollow tube were identical to those used in Comparative Example 1 except that the extrusion molding was carried out using a mandrel having projections at 4 positions thereon. The hollow tube is thus provided with 4 grooves. Both of the width and depth of the groove are equal to 0.05 mm. The tube has an inner diameter of 0.80 mm and a thickness of 0.35 mm (including the depth (0.05 mm) of the inner groove). The hollow tube was treated by the same method used in Comparative Example 1 to give sustained release dispensers each having a length of 200 mm and containing 80 mg of HDDA enclosed therein.

The ingredient-release quality of the dispenser was examined in the same manner used in Example 1. The results thus obtained are plotted on FIGS. 3 and 4. As seen from FIGS. 3 and 4, the ingredient-release quality of the dispenser slightly approached that of the sustained release dispenser produced in Comparative Example 1. The rate of the remaining HDDA observed after 60 days was found to be 15%.

EXAMPLE 4

There was charged Z-8-dodecenyl acetate (hereunder referred to as "DDA"), i.e., the sex pheromone of Grapholita molesta Busck as a harmful insect for fruits in a polyethylene bottle whose inner layer was a porous layer produced by foam molding. The bottle was a cylindrical one having an outer diameter of 7.0 mm and a length of 15.0 mm and produced by simultaneously extrusion-molding a polyethylene for the inner layer containing azodicarbonamide as a foaming agent and a polyethylene for the outer layer. The resulting bottle had a thickness of 0.25 mm (including the porous layer having a thickness of 0.05 mm). There was charged 240 mg of DDA in the 0.50 m volume bottle thus produced and then the opening for charging was sealed to give a sustained release dispenser.

Figure 5:
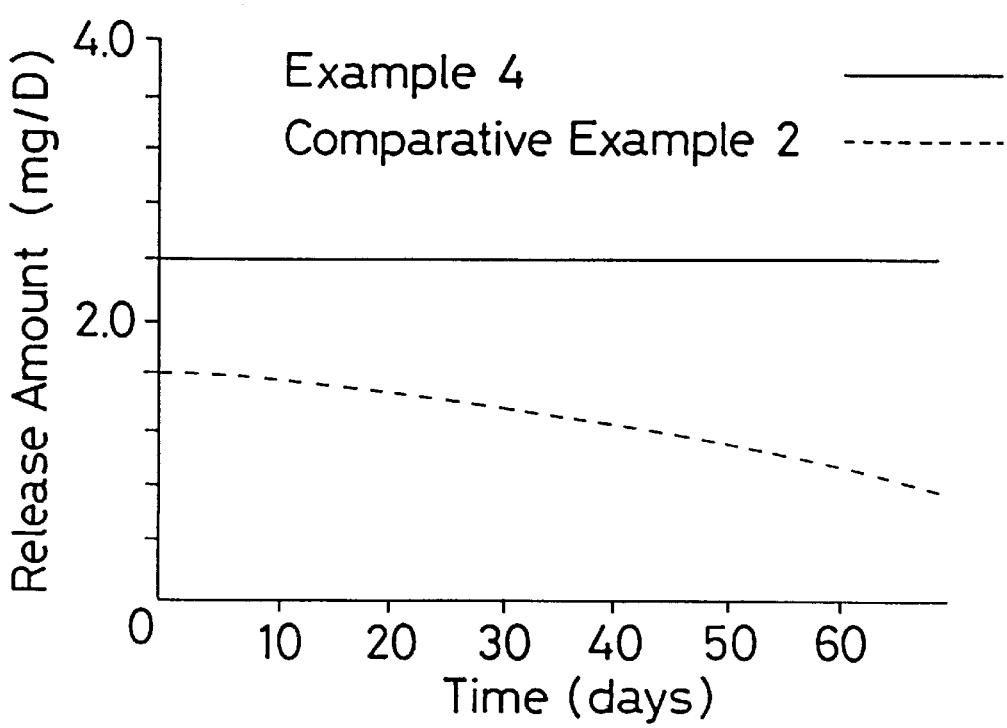
FIG. 5 is a diagram showing a change, with time, of the amount of released DDA.

The dispenser was introduced into a thermostatic chamber maintained at 40° C. to determine the ingredient-release quality of the dispenser. The results thus obtained are plotted on FIG. 5. FIG. 5 is a diagram showing a change, with time, of the amount of the released DDA. There was not observed any change in the amount of released DDA throughout the test. The rate of remaining DDA observed after 60 days was found to be 40%.

COMPARATIVE EXAMPLE 2

There was charged DDA in a bottle whose inner wall was smooth. The conditions for producing the bottle were identical to those used in Example 4 except that the extrusion molding was carried out using a polyethylene free of any foaming agent. After charging 240 mg of DDA into the cylindrical bottle having an outer diameter of 7.0 mm, a length of 15.0 mm, a thickness of 0.20 mm and a volume of 0.51 m, the opening for charging was sealed to give a sustained release dispenser.

The ingredient-release quality of the dispenser was examined in the same manner used in Example 4. The results thus obtained are plotted on FIG. 5. As seen from FIG. 5, the amount of the released ingredient was small from the initiation of the test and reduced with time. The rate of the remaining DDA observed after 60 days was found to be 66%.

EXAMPLE 5

There was used, as the liquid permeable film 7, a double-layered film comprising a low density polyethylene (LDPE) film having a thickness of 40 μm and a biaxially oriented polypropylene (OPP) film having a thickness of 30 μm. Then two three-layered laminate sheets each was prepared by putting a highly wettable film 8 of a polypropylene non-woven fabric having a surface area of 6 cm² and a thickness of 75 μm on the LDPE side of the double-layered film except for the portion 10 at which the permeable film 1 was ultimately sealed. A bag was prepared from these two laminate sheets, followed by injecting, into the bag, 100 mg of a liquid sex pheromone 9, i.e., Z-11-tetradecenyl acetate as a sex pheromone component of oriental tea tortrix (Homona magnanima Diakonoff) to give a sustained release dispenser wherein highly wettable films 8 were set up on both sides (having an overall surface area of 12 cm²) of the inner wall of the bag.

Figure 8:
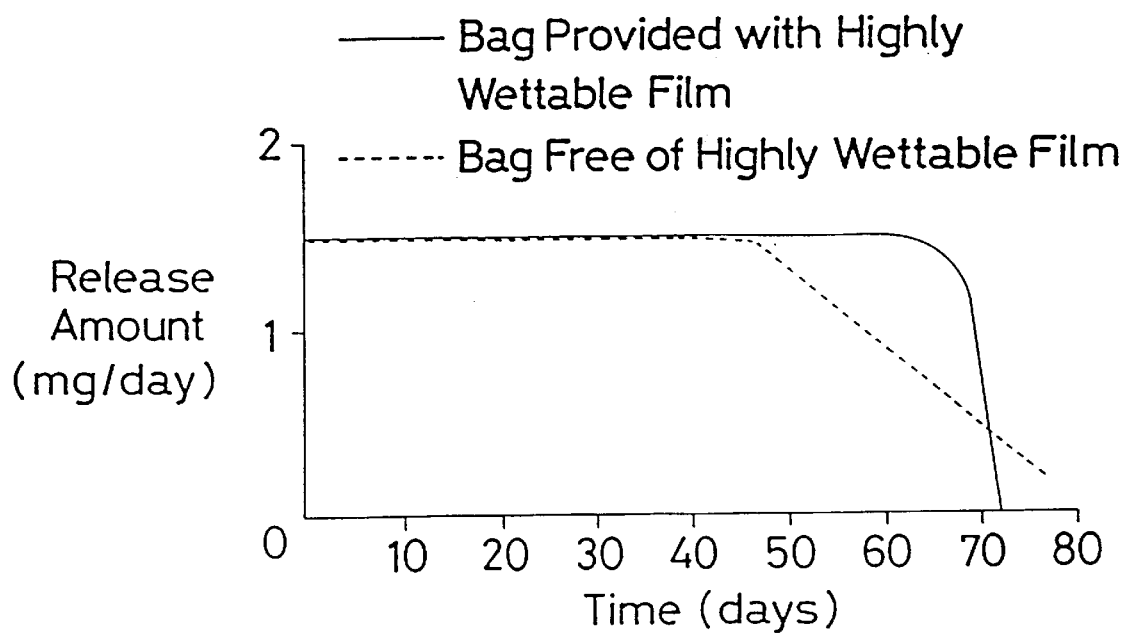
FIG. 8 is a diagram showing a change, with time, of the amount of pheromone released.

The resulting sustained release dispenser was allowed to stand under the conditions of a temperature of 30° C. and a wind velocity of 0.5 m/sec to determine the change, with time, in the amount of Z-11-tetradecenyl acetate released from the dispenser. The results thus obtained are plotted on FIG. 8 as a solid line (specified as "Bag Provided with Highly Wettable Film"). The data plotted on FIG. 8 clearly indicate that the dispenser could maintain a uniform released amount of the pheromone on the order of 1.5 mg/day over not less than 60 days.

By way of comparison, a comparative sustained release dispenser was also prepared by producing a bag from only two double-layered sheets comprising an LDPE film having a thickness of 40 μm and an OPP film having a thickness of 30 μm without using any highly wettable film 8, followed by injecting 100 mg of Z-11-tetradecenyl acetate as the liquid sex pheromone 9. The comparative dispenser was likewise be allowed to stand under the conditions of a temperature of 30° C. and a wind velocity of 0.5 m/sec to determine the change, with time, in the amount of Z-11-tetradecenyl acetate released from the resulting dispenser. The results thus obtained are plotted on FIG. 8 as a chain line (specified as "Bag Free of Highly Wettable Film"). As seen from FIG. 8, the comparative dispenser maintained a uniform release rate of 1.5 mg/day over 45 days, but the release rate thereof was then gradually reduced.

The sustained release dispenser according to the present invention allowed uniform release of a volatile liquid ingredient over a long time period even when the amount of the liquid ingredient remaining in the container was reduced and therefore, the ingredient could be used without waste. The sustained release dispenser ensured a uniform release rate over a long period of time and hence efficient mating disruption of harmful insects.

What is claimed is:

1. A sustained release dispenser comprising a plastic container, which accommodates a liquid and volatile ingredient therein, wherein the plastic container essentially consists of an outer layer permeable to the liquid and volatile ingredient and an inner layer having liquid-absorbing pores capable of communicating with one another for maintaining the absorption of the volatile ingredient at a constant wetting level, and the inner layer and the outer layer are produced from the same kind of plastics.

2. The sustained release dispenser as set forth in claim 1 wherein the outer and inner layers are formed from at least one compound selected from the group consisting of polyolefins, ethylene-vinyl acetate copolymers, ethylene-acrylic acid ester copolymers and ethylene-methacrylic acid ester copolymers.

3. The sustained release dispenser as set forth in claim 1 wherein the volatile ingredient is a sex pheromone.

* * * * *